(12) United States Patent
Larsen et al.

(10) Patent No.: US 7,335,154 B2
(45) Date of Patent: Feb. 26, 2008

(54) RADIOTHERAPY

(75) Inventors: Roy Larsen, Oslo (NO); Gjermund Henriksen, Oslo (NO)

(73) Assignee: Algeta AS, Oslo (NO)

( * ) Notice: Subject to any disclaimer, the term of this patent is extended or adjusted under 35 U.S.C. 154(b) by 0 days.

(21) Appl. No.: 11/337,385

(22) Filed: Jan. 23, 2006

(65) Prior Publication Data

US 2006/0135842 A1 Jun. 22, 2006

Related U.S. Application Data

(63) Continuation of application No. 10/332,056, filed as application No. PCT/GB01/02996 on Jul. 4, 2001, now Pat. No. 7,056,275.

(30) Foreign Application Priority Data

Jul. 4, 2000 (NO) .................................. 20003457

(51) Int. Cl.
*A61N 5/00* (2006.01)

(52) U.S. Cl. .......................................................... 600/3

(58) Field of Classification Search ................ 600/1–8; 128/897–898
See application file for complete search history.

(56) References Cited

U.S. PATENT DOCUMENTS

| | | | |
|---|---|---|---|
| 2,329,147 A | 9/1943 | Troch et al. | |
| 4,560,548 A | 12/1985 | Simon et al. | |
| 5,192,526 A | 3/1993 | Pipes | |
| 5,902,825 A | 5/1999 | Jia | |
| 6,548,042 B2 | 4/2003 | Arstad et al. | |
| 6,592,843 B2 | 7/2003 | Larsen et al. | |
| 6,635,234 B1 | 10/2003 | Larsen et al. | |
| 6,740,304 B2 | 5/2004 | Larsen et al. | |
| 7,056,275 B2 * | 6/2006 | Larsen et al. .................. | 600/3 |
| 2003/0023050 A1 | 1/2003 | Frank et al. | |
| 2003/0086868 A1 | 5/2003 | Ma et al. | |
| 2003/0166989 A1 | 9/2003 | Larsen et al. | |
| 2003/0206857 A1 | 11/2003 | Larsen et al. | |
| 2004/0009955 A1 | 1/2004 | Larsen et al. | |
| 2004/0184990 A1 | 9/2004 | Larsen et al. | |
| 2004/0208821 A1 | 10/2004 | Larsen et al. | |
| 2006/0228297 A1 | 10/2006 | Larsen et al. | |

FOREIGN PATENT DOCUMENTS

| | | |
|---|---|---|
| WO | WO 00/40275 | 7/2000 |
| WO | WO 00/76556 | 12/2000 |
| WO | WO 01/66155 | 9/2001 |

OTHER PUBLICATIONS

Beyer et al., "Simultaneous Study of the Biodistribution of Radio-Yttrium Complexed with EDTMP and Citrate Ligands in Tumour-Bearing Rats," *International Journal of Radiation Applications and Instrumentation. Part B, Nuclear Medicine and Biology*, 19:201-203 (1992).
Cabell, "The Purification, Determination, and Neutron Capture Cross Section of Actinium-227," *Can. J. Chem.* 37:1094-1103 (1959).
Davis et al., "Comparison of $^{225}$Actinium Chelates: Tissue Distribution and Radiotoxicity," *Nucl. Med. Biol.* 26:581-589 (1999).
Deal et al., "Improved In Vivo Stability of Actinium-225 Macrocyclic Complexes," *J. Med. Chem.* 42:2988-2992 (1999).
Feinendegen and McClure, "Alpha-Emitters for Medical Therapy—Workshop of the United States Department of Energy" *Radiat. Res.* 148:195-201 (1997).
Kaspersen et al., "Cytotoxicity of $^{213}$Bi- and $^{225}$Ac-immunoconjugates," *Nucl. Med. Commun.* 16:468-476 (1995).
McClure and Feinendegen, "Alpha Emitters for Medical Therapy: Second Bi-Annual Workshop", Toronto, Canada, Jun. 4-5, 1998, DOE/NE-0116, pp. 1-25, U.S. Department of Energy, 19901 Germantown Road, Germantown, MD 20874, USA.
Müller, "Präparative Arbeiten über $^{227}$Ac und seine Folgeprodukte I. Trenn- und Meβverfahren," *Radiochimica Acta* 9:181-186 (1968) (English language abstract).
U.S. Appl. No. 11/665,197; Larsen et al., filed Apr. 12, 2007.
U.S. Appl. No. 10/588,839; Salberg et al., filed Aug. 8, 2006.
Parrington et al., "Nuclides and Isotopes," 15th Ed., General Electric Co. and KAPL, Inc., 1996, p. 11, 16, 46.

* cited by examiner

*Primary Examiner*—Samuel G. Gilbert
(74) *Attorney, Agent, or Firm*—Clark & Elbing LLP

(57) ABSTRACT

The invention provides a method of radiation treatment of a human or non-human mammalian subject which comprises administering to said subject a therapeutically, prophylactically or pain-palliating amount of a bone targeting complex of an alpha-particle emitting thorium or actinium radionuclide, e.g. for the treatment of calcified tumors, bone tumors, bones, bone surfaces and soft tissues.

12 Claims, No Drawings

RADIOTHERAPY

CROSS REFERENCE TO RELATED APPLICATIONS

The present application is a continuation of U.S. patent application Ser. No. 10/332,056, filed Mar. 24, 2003, now U.S. Pat. No. 7,056,275 which is the U.S. National Stage of PCT/GB01/02996, filed on Jul. 4, 2001, and which, in turn, claims the benefit of Norwegian patent application number NO 20003457, filed on Jul. 4, 2000.

The present invention relates to a method of therapeutic, prophylactic or pain-palliative treatment of a mammalian subject which involves administering to the subject a complex of an alpha-particle emitting thorium or actinium isotope, to the use of alpha-particle emitting thorium or actinium isotopes in the manufacture of medicaments for use in such treatment, and to such medicaments.

A substantial percentage of cancer patients are affected by skeletal metastases and as many as 85% of patients with advanced lung, prostate and breast carcinoma develop bone metastases. Established treatments, such as hormone therapy, chemotherapy and external radiotherapy, often cause a temporary response, but ultimately most cancer patients with bone metastases experience relapses.

The use of radionuclides for pain palliation and/or cancer treatment for skeletal lesions has previously involved low linear energy transfer (LET) radiation emitters (i.e. beta emitters), and also conversion electron emitters. Such bone targeting radio-pharmaceuticals have been included in clinical trials, and two products, namely strontium-89 (Metastron™) and samarium-153-EDTMP (Lexidronam™), have recently been approved for pain palliation of skeletal metastases. However, because of the tissue penetration range of the radiation, such low LET emitters can only be administered in amounts sufficient for pain palliation rather than in the higher amounts required for tumor therapy, because significant myelotoxicity occurs before an effective antitumor therapeutic dose level can be reached.

Bone-seeking radioactive chelates have previously been described for several beta-emitters and for the alpha-emitter bismuth-212, as well as the in vivo generator system lead-212/bismuth-212. As mentioned above, the beta-emitting bone-seekers have demonstrated effective pain relief in a significant fraction of patients with skeletal metastases from prostate and breast cancers, but they have the draw-back that suppression of bone-marrow occurs before therapeutic dose levels are reached. The $^{212}$Pb/$^{212}$Bi based compounds have two main problems that reduce their clinical potential. Firstly, $^{212}$Bi itself has a very short half life ($t_{1/2}$ 60.6 min) and therefore a large fraction of the administered dose decays before localization in bone and clearance from soft tissues occurs, resulting in an unwanted degree of soft tissue exposure. Secondly, when the $^{212}$Pb mother nuclide ($t_{1/2}$=10.6 h), which is a beta-emitter, combined with a bone-seeking carrier is used as an in vivo generator for $^{212}$Bi, a significant fraction of $^{212}$Bi translocates in vivo, resulting among other things in an undesirably elevated kidney exposure.

Thus, there is a strong need for new therapies to relieve pain and slow down tumor progression.

We have now found that alpha-particle emitting actinium and thorium radionuclides can be efficiently targeted to the bone surface when complexed to form bone-targeting complexes, e.g. chelate complexes, and so deliver therapeutically, prophylactically or pain-palliative radiation doses at the bone surface without causing undesirably high radiation exposure to soft tissue organs such as kidney, liver and spleen. As alpha-emitters, these radionuclides are superior to the conventionally used beta-emitters since the shorter penetration range of the alpha particle means that the exposure of the bone marrow to radiation is less. Thus for example dosimetric calculations indicate that, in the mouse model, the bone surface to bone marrow dose ratio is approximately three times higher with the bone-targeting alpha-emitters than with bone-targeting beta-emitters.

Thus viewed from one aspect the invention provides a method of radiation treatment of a human or non-human mammalian subject (e.g. a human, canine or murine subject) which comprises administering to said subject a therapeutically, prophylactically or pain-palliating amount of a bone-targeting complex of a radionuclide, the improvement comprising using as said radionuclide a radionuclide selected from the group consisting of alpha-particle emitting thorium and actinium radionuclides.

Viewed from a further aspect the invention provides the use of an alpha particle emitting thorium or actinium radionuclide, or a bone-targeting complex thereof, for the manufacture of a medicament for use in a method of radiation treatment of a human or non-human mammalian subject which comprises administering to said subject a bone-targeting complex of said radionuclide.

Viewed from a still further aspect the invention provides a radiopharmaceutical composition comprising a bone-targeting complex of a radionuclide selected from alpha-particle emitting thorium and actinium radionuclides, together with at least one physiologically acceptable carrier or excipient.

Viewed from a still further aspect the invention provides a bone-targeting complex of a radionuclide selected from alpha-particle emitting thorium and actinium radionuclides, especially for use in medicine.

By bone-targeting (or bone-seeking), it is meant that the radionuclide complex distributes preferentially to the bone as opposed to soft tissue organs, in particular kidney, liver and spleen, e.g. more preferentially than the acetate salt of the radionuclide. Preferably the distribution ratio (e.g. measured by radiation emission detection in the mouse (e.g. Balb/C mouse) model four hours after intravenous administration) is at least 3, more preferably at least 8, especially at least 15, for femur to liver, and/or at least 4, more preferably at least 5, especially at least 5.5, for femur to kidney, and/or at least 5, more preferably at least 15, especially at least 25, for femur to spleen.

The complexes used according to the invention are complexes with any appropriate complexing, e.g. chelating, agent which serves to target the complex to the bone. Phosphonic acid complexants, especially bisphosphonate and polyphosphonate complexants, are especially preferred, e.g. phosphonic acid analogs of the polycarboxylic acid complexants proposed as carriers for paramagnetic nuclei (such as Gd and Dy) in magnetic resonance imaging contrast agents. Such polycarboxylic acid complexants are widely discussed in the patent literature of Nycomed, Schering, Mallinckrodt, Bracco and Guerbet. Suitable examples of such phosphonic acid analoges include diethylenetriamine-N,N',N"-pentamethylene-phosphonic acid (DTMP) and 1,4,7,10-tetraazacyclodocecane-1,4,7,10-tetramethylenephosphonic acid (DOTMP), i.e. analogs of DTPA and DOTA respectively.

The radionuclides are preferably thorium-227 and actinium-225; however other alpha-emitting thorium and actinium radionuclides can also be used, e.g. thorium-225, thorium-226, thorium-228, actinium-223 and actinium-224.

The thorium and actinium radionuclides may be used separately, or in combination with each other, or with other radionuclides, e.g. alpha or beta emitters.

The present invention thus relates to a novel use of radioisotopes of actinium and thorium, e.g. actinium-225 and thorium-227, combined with bone-seeking chelator molecules for the treatment of bone surfaces and bone related malignant and non-malignant diseases. These elements have radioisotopes with half lives of several days, which reduces the risk of translocation compared to isotopes with shorter half lives.

We have found that alpha emitters with different chemical properties, but with similar half lifes, can be incorporated into bone. Although bone deposition has been reported for other heavy elements, accumulation in some soft tissues would prevent these from being used biomedically in their cationic forms. However, we found that thorium and actinium can be carried to, and incorporated into, bone surfaces in the form of bone seeking chelates. Such chelates generally have a quite rapid clearance from soft tissues. Furthermore, the stability of the radiolabeled compounds was biomedically relevant, as indicated by excellent bone to soft tissue ratios 4 hours after injection, and that promising bone to normal tissue distribution ratios could be achieved. Alpha cascade emitter series originating from, for example, actinium-225 and thorium-227, can thus be incorporated into bone surfaces and used to treat bone surfaces and osseous tumors, as well as other bone related diseases. To our knowledge we are the first to describe the preparation and use of bone-seeking radioactive chelates carrying the elements actinium and thorium.

During the work of the present application the inventors made the significant and unexpected discovery that it is possible to prepare actinium- and/or thorium-based radioactive chelates with sufficient in vivo stability for bone surface targeting. This was unexpected because attempts to conjugate similar types of chelators to monoclonal antibodies had failed to produce radiolabeled products with sufficient stability. Some preclinical data exist about the use of chelates of actinium-225 conjugated to monoclonal antibodies for cancer therapy, but the data indicated insufficient stability in vivo for the compounds tested (see Davis, et al., Nucl. Med. Biol. 26: 581-589 (1999); Deal et al., J. Med. Chem. 42: 2988-2992 (1999); Feinendegen et al., Radiat. Res. 148: 195 (1997); and McClure et al., "Alpha emitters for medical therapy: Second bi-annual workshop", Toronto, Canada, Jun. 4-5, 1998, DOE/NE-0116, U.S. Department of Energy, 19901 Germantown Road, Germantown, Md. 20874, USA). In addition, none of the chelates tested were bone-seekers (see Davis et al., (supra); Deal et al., (supra); and Kaspersen et al., Nucl. Med. Commun. 16: 468-476 (1995)). The use of thorium in molecular tumor targeting or bone surface targeting has to the inventors' knowledge not been suggested previously and forms a further aspect of the invention.

The isotopes used according to the present invention typically have half lives of several days (e.g. $^{227}$Th ($t_{1/2}$=18.7 days) and $^{225}$Ac ($t_{1/2}$=10.0 days)) which may secure a better (through biosynthesis) incorporation of radiopharmaceutical in the bone matrix before decay occurs, thereby reducing translocation of daughter radionuclides. Furthermore, the decay of the radioactive series may release up to 4 alphas for actinium (e.g. actinium-225) and 5 alphas for thorium (e.g. thorium-227), i.e. emissions of cascades of highly cytotoxic alpha particles will occur in the target area.

The compounds used in accordance with the invention may be prepared by mixing a bone seeking chelating and/or complexing agent with thorium and/or actinium radionuclides, with or without a subsequent purification of the radiopharmaceutical. If desired, a radiolabeled chelate can first be prepared and then subsequently conjugated to a molecule with affinity for calcified tissues. Purification of the final products may be effected using ion exchange procedures.

Thus this method of production may be a method to prepare bone-seeking chelates and/or complexes containing an actinium and/or thorium radioisotope, or a combination of these, for biomedical uses, characterised in combining radioisotope(s) with a chelating and/or complexing molecule with bone affinity, with or without subsequent purification of the product(s).

As mentioned above, the bone-seeking carriers used with the thorium and/or actinium radioisotope(s) could be from the general class of bone seeking chelating and/or complexing molecules including, but not limited to, the more specific class of bisphosphonates and polyphosphonates.

The present invention thus discloses the use of actinium and/or thorium radioisotope(s) combined with bone seeking chelator(s) and/or complexing agent(s) to produce a pharmaceutically active preparation to treat diseased bone, including malignancies and bone surfaces. The following Examples show a high and selective uptake of actinium and thorium when combined with bone seeking chelators. These compounds can be used to irradiate the bone surfaces with alpha-particles to inactivate microscopic deposits of cancer cells on the bone surfaces, as well as to treat larger osseous tumor lesions. Compared to the commonly used beta-emitters and conversion election emitters, the use of these alpha emitting compounds can significantly reduce the dose to red bone marrow, i.e. myelotoxicity is reduced.

The present invention further discloses the use of a preparation according to the present invention in a combination therapy with another therapeutically active component, or several components, such as, but not limited to, chemotherapy including bisphosphonates, surgery, external beam irradiation, low-LET radiation emitting bone seeking radiopharmaceuticals, and/or hormonal treatment. Furthermore, when a preparation according to the present invention is used for therapy and/or palliation related to non-malignant and/or malignant diseases affecting bones and/or soft tissues, the malignant diseases in question may be diseases selected from the group consisting, but not limited to, prostate cancer, breast cancer, kidney cancer, kidney and urinary cancer, primary bone cancer, lung cancer and multiple myeloma.

A preparation according to the present invention may further be used in a method for prophylactic or therapeutic treatment of non-malignant and/or malignant disease affected bones and soft tissues in a mammal (such as a dog or a human), comprising administrating to the mammal in need thereof, a palliative or therapeutically effective amount of the preparation.

The preparation may be for example a physiologically acceptable preparation for intravenous, per oral, subcutaneous or intraperitoneal administration, characterised in comprising a bone seeking chelate including an actinium or thorium radioisotope or a combination of those, with or without agent(s) to prevent precipitation and/or generation of colloids, in addition to pharmacologically acceptable carriers and adjuvants.

The bone seeking chelate(s) carrying thorium and/or actinium, optionally in salt form with a physiologically tolerable counterion (e.g. sodium, calcium, meglumine, etc.) may be administered to a mammal (such as a dog or a human in need thereof), by any convenient administration route, such as oral, subcutaneous, intravenous, intraarterial or transcutaneous. Preferably administeration is parenteral by injection or infusion.

Appropriate oral administration forms include tablets, capsules, powders, or liquids (such as suspensions, solutions, syrups or emulsions). When formed into tablets, conventional expicients, lubricating agents and/or binding agents may be used. When administered as injection or infusion solutions, the carrier is preferably isotonic saline, with or without agent(s) to stabilize the chelate(s) to prevent precipitation of chelator salts or insoluble complexes, and/or to prevent the generation of colloids.

The active principle according to the present invention could be used both in prophylactic, palliative and therapeutic treatment of non-malignant and/or malignant diseases affecting bones and soft tissues. The malignant diseases may be selected from the group consisting of, for example, prostate cancer, breast cancer, kidney and urinary cancer, primary bone cancer, lung cancer and multiple myeloma, and the non-malignant diseases may be selected from the group consisting of autoimmune diseases affecting joints and the skeleton, e.g. rheumatoid arthritis, schleroderma and spodyloarthropathies.

The physiologically acceptable preparation for in vivo administration according to the present invention typically comprises a dissolved complex (e.g. a salt of the chelator complex with the radionuclides), with or without agents to prevent precipitation and/or prevent colloid formation, in addition to pharmacologically acceptable carriers and adjuvants. The concentration of the active compounds in the preparation will generally be less than the individual $LD_{50}$ dose, for example less than 20% of the $LD_{50}$ dose, and thus will vary for the different components. The activity of the radionuclides will depend upon several factors, e.g. half life, energy released, route of administration and the underlying condition or disease, and the dosage will vary between approximately 10 kBq-2 MBq per kg bodyweight administered in single or multiple doses to mammals, such as for example humans.

The present invention further relates to a kit for the preparation of physiological compatible solutions containing actinium and/or thorium radioisotope(s) and pharmaceutical acceptable carriers, for the treatment of bone surfaces, primary and/or metastatic cancers to the skeleton etc, and with or without suitable administration equipment. Thus viewed from a further aspect the invention provides a kit for the treatment of bone surfaces, or primary and/or metastatic cancers to the skeleton, comprising: an alpha-particle emitting actinium or thorium radioisotope and a bone seeking chelator, for the preparation of physiologically compatible solutions of an actinium or thorium radioisotope chelate; a pharmaceutically acceptable carrier; and, optionally, administration equipment.

The present invention will now be described with reference to the following non-limiting Examples.

The following shows the main branch of the actinium-225 and its daughters' decay series (half life and mode of decay in brackets):

$^{225}$Ac (10.0 d., α) $^{221}$Fr (4.8 min., α) $^{217}$At (0.032 s., α) $^{213}$Bi (47 min., β) $^{213}$Po (4.2 μs., α) $^{209}$Pb (3.3 h, β) $^{209}$Bi (stable)

The following shows the main branch of the thorium-227 and its daughters decay series (half life and mode of decay in brackets):

$^{227}$Th (18.7 d., α) $^{223}$Ra (11.4 d., α) $^{219}$Rn (3.9 s., α) $^{215}$Po (1.8 ms., α) $^{211}$Pb (36.1 min., β) $^{211}$Bi (2.15 min, α) $^{207}$Tl (4.8 min., β) $^{207}$Pb (stable)

The actinium experiments reported below were performed with actinium-228. Identical chemistry of $^{225}$Ac and $^{228}$Ac can reasonably be assumed since isotopic effects are likely to be minimal because of the low relative weight difference (about 1.3%) between these two isotopes. All thorium experiments were performed with thorium-227.

TABLE 1

γ-rays and their probabilities in the decay of $^{227}$Th and $^{225}$Ac. Only the most abundant γ-ray is listed for each radionuclide.

| Thorium-227 | 118.7 d | 235.9 keV (12.3% probability) |
| Actinium-228 | 6.13 h | 911.2 keV (26.6% probability) |

Materials

The $^{232}$Th(NO$_3$)$_4$ and the $^{227}$Ac-oxide used in this work had been stored for more than 20 years. Two different batches of $^{223}$Th(NO$_3$)$_4$ were used, i.e. (1) Th(NO$_3$)$_4$.6H$_2$O (Fluka AG Buchs SG, Switzerland, and (2) Th(NO$_3$)$_4$.4H$_2$O (J.L Baker Chemical Co, Phillisburg, N.J., USA). The $^{227}$Ac was derived from a 28 years old $^{231}$Pa source. The samples were provided by Nuclear Chemistry Group, Department of Chemistry, University of Oslo, Oslo, Norway.

Ion exchange resins were supplied by Bio-Rad (Hercules, Calif., USA).

The ion exchange resins were preconditioned by washing with water, then 7M HCl, followed by acetone, and finally with water. The resins were stored in water prior to column packing.

The Amberlite XAD7-HP resin was purchased from Rohm & Haas (Frankfurt, Germany). The resin was treated with 2M HNO$_3$ prior to use.

Methods $^{227}$Th was isolated from a $^{227}$Ac-decay mixture by anion exchange chromatography in a nitrate solution as described by Müller in Radiochimica Act 9: 181-186 (1968) and hereby incorporated by reference. In preparation for the chelating step, the eluate containing $^{227}$Th was evaporated to dryness. Thereafter, $^{227}$Th was dissolved in 0.1M HNO$_3$.

EXAMPLE 1

$^{228}$Ac-Preparation $^{228}$Ac was produced by a combination of solvent extraction and ion exchange.

Solvent extraction procedure for Th/Ra separation:

$^{228}$Ra intended for use as generator material for $^{228}$Ac was isolated by extraction from $^{232}$Th. 15-20 g quantities of $^{232}$Th(NO$_3$)$_4$ hydrate was dissolved in 20 ml 0.1M HNO$_3$, added to a 250 ml separation funnel, and contacted with 3×70 ml of a 2M solution of di(2-ethylhexyl)orthophosphoric acid) (HDEHP) in heptane. The combined aqueous phases from four extraction batches, each produced from the extraction procedure on 15-20 g $^{232}$Th(NO$_3$)$_4$ hydrate, were washed three times with 30 ml heptane. After this, the aqueous solution was evaporated to 10 ml. Thereafter, two extractions of the solution with 20 ml heptane were done. In preparation for the ion exchange procedure, the solution was eluted through a column of Amberlite XAD-7HP resin for removing residual organic components.

EXAMPLE 2

Ion Exchange Procedure for Ra/Ac Separation

An example of Ac/Ra separation employing strong cation exchange resins is described by Cabell in Can. J. Chem. 37: 1094-1101 (1959) and hereby incorporated by reference. The solution containing $^{228}$Ra and $^{228}$Ac, obtained as described above, was applied to a 3×50 mm column of AG50W-X12. The column was washed with 10 ml 1M HNO$_3$. $^{212}$Pb, $^{212}$Bi, $^{224}$Ra and $^{228}$Ra were thereafter eluted with 3M HNO$_3$ and the solution was left for one month in order to allow coeluted $^{224}$Ra to decay.

For preparation of $^{228}$Ac sources, the solution containing $^{228}$Ra in 3M HNO$_3$ was evaporated to dryness. The radionuclide was leached from the vessel using 1 ml 1M HNO$_3$. This solution was applied to a 3×40 mm column of AG50W-X12. Again, $^{228}$Ra was eluted in 3M HNO$_3$. $^{228}$Ac was eluted in 6M HNO$_3$, the solution was then evaporated to dryness and dissolved in 0.1M HNO$_3$ in preparation for the chelation chemistry step.

EXAMPLE 3

Preparation of Coordination Compounds 20-30 μl of a 50 mM aqueous solution of DTMP or DOTMP, adjusted to pH 5-5.5 with CH$_3$COONH$_4$, was added to the radionuclides in 50-100 μl of 0.05-0.1M HNO$_3$. pH was adjusted to 5-5.5 with CH$_3$COONH$_4$ and the reaction mixture was brought to 60° C. for 10 h (for thorium) or 1 h (for actinium). Thereafter, each radionuclide complex was eluted on a 2×20 mm column of Chelex-100 cation exchange resin. Above 80% of the $^{227}$Th eluted from the column, while the corresponding values for $^{228}$AC was 50-60% (decay corrected).

Solutions for injection were prepared by diluting the complexes in a 0.1M sodium N morpholine ethane sulphonate (NaMES) buffer followed by filtration through sterile 0.22 μm syringe filters (Nylon membrane, 5 mm diameter Whatman, Maidstone, UK).

Preparation of $^{227}$Th in CH$_3$COONH$_4$/MES-Solution $^{227}$Th for injection as a weakly complexed cation, was prepared by neutralizing the 0.1M HNO$_3$ solution with CH$_3$COONH$_4$, thereafter the solution was diluted to the desired activity concentration with 0.1M MES buffer followed by sterile filtration.

EXAMPLE 4

Biodistribution Experiments

The biodistribution of thorium and actinium bound to polyphosphonate was studied in mice.

Balb/C mice with a bodyweight in the range of 11-16 g were used in the biodistribution experiments. The compounds were administered by intravenous injection of 100-200 μl of the preparation for each animal in paired label arrangement. The compounds $^{228}$Ac-DOTMP, $^{227}$Th-DOTMP, $^{227}$Th-DTMP and $^{227}$Th-acetate/MES were investigated. Approximately 5 kBq of $^{228}$Th and 5 kBq of $^{228}$Ac was injected. Animals were sacrificed by cervical dislocation. The tissue distribution was determined on 3 mice for each pair of compounds. The tissue distribution was determined after 4 hours for $^{228}$Ac-DOTMP, $^{227}$Th-DOTMP, $^{227}$Th-DTMP and $^{227}$Th-acetate.

In general, radioactivity in the tissue samples was measured by using a NaI (Tl) well-type detector and by liquid scintillation counting (Beckmann LS6500, Beckmann, Fullerton, Calif., USA). $^{227}$Th was measured by using a HPGe detector (Canberra, Conn., USA) and also by liquid scintillation counting after dissolution of tissue samples and allowing decay of $^{228}$Ac. $^{228}$Ac was measured by the HPGe detector and the NaI (Tl) detector.

Samples of the radioactive preparations of the nuclides were used as references to account for physical decay and radiation crossover in the detection procedures.

TABLE 2

Tissue distribution of bone seekers 4 hours after injection (% I.D./g +/− SD)

| | Th-227 DTMP | Ac-228 DOTMP | Th-227 DOTMP |
|---|---|---|---|
| Blood | <0.1 | <0.1 | <0.1 |
| Kidney | 1.38 ± 0.54 | 2.7 ± 2.4 | 3.43 ± 1.70 |
| Liver | 0.40 ± 0.43 | 1.26 ± 0.9 | 0.39 ± 0.19 |
| Femur | 19.58 ± 3.58 | 20.67 ± 2.23 | 20.55 ± 2.21 |
| Skull | 12.3 ± 3.14 | 10.7 ± 2.7 | 10.8 ± 2.94 |
| Rib | 8.83 ± 5.06 | 10.5 ± 3.5 | 11.06 ± 3.81 |
| Lung | 0.12 ± 0.04 | 0.20 ± 0.10 | 0.18 ± 0.09 |
| Muscle | 0.63 ± 0.33 | 0.30 ± 0.11 | 0.29 ± 0.17 |
| Heart | <0.1 | <0.1 | <0.1 |
| Brain | <0.1 | <0.1 | <0.1 |
| S.I. | 0.56 ± 0.63 | 0.14 ± 0.07 | 0.14 ± 0.08 |
| L.I. | 0.15 ± 0.03 | 0.20 ± 0.11 | 0.19 ± 0.10 |
| Spleen | 0.13 ± 0.04 | 0.51 ± 0.10 | 0.51 ± 0.14 |
| Stomach | 0.70 ± 0.80 | 0.20. ± 0.10 | 0.15 ± 0.05 |
| Urine | N.A. | N.A. | 21.1 (n = 1) |

N.A. Data not available

The data in Table 2 show that the polyphosphonates carrying actinium and thorium show excellent bone to soft tissues ratios indicating suitable stability of the chelator radionuclide complex for in vivo targeting. The bone samples from femur, skull and ribs all show much higher uptake than the soft tissue organs studied.

Data for the dissolved acetate salt of thorium-227 is presented in Table 3. As can be seen, the bone uptake of cationic thorium is high and similar to the observed values with the bone-seeking polyphosphonate complexing agents; however the affinity for some soft tissues, e.g. the liver and spleen, makes this material unsuitable for in vivo bone targeting.

TABLE 3

Tissue distribution of $^{227}$Th-acetate (% I.D./g +/− SD) 4 hours after injection (n = 2)

| | |
|---|---|
| Blood | 1.2 ± 0.4 |
| Kidney | 7.7 ± 0.7 |
| Liver | 56.5 ± 9.4 |
| Femur | 23.4 ± 6.9 |
| Skull | 18.9 ± 7.6 |
| Rib | 14.6 ± 4.4 |
| Lung | 2.6 ± 0.4 |
| Muscle | 1.1 (n = 1) |
| Heart | 2.6 ± 0.2 |
| Brain | <0.1 |
| S.I | 2.3 ± 0.1 |
| L.I. | 1.7 ± 0.1 |
| Spleen | 14.2 ± 2.8 |
| Stomach | 4.6 ± 1.0 |

Data for biodistribution of cationic actinium in mice has recently been published (see Davis et al., (supra); and Deal et al., (supra)) and reveal that this element, as a cationic species (i.e. the dissolved salt of actinium acetate) also does not show sufficient selective bone uptake relative to soft tissue uptake to be suitable as a therapeutic bone seeker by itself.

Compared to cationic radium-223 at 6 hours after injection (see Table 4), thorium-227-DTMP, thorium-227-DOTMP and actinium-228-DOTMP at 4 hours after injection, showed better femur to blood and femur to tissue ratios for some organs even though the radium had had more time for clearance from soft tissues.

TABLE 4

Femur to soft tissue ratios for cationic radium-223 compared with bone seeking chelates of actinium-228 and thorium-227 in Balb C mice.

|  | $^{223}$Ra | $^{228}$Ac-DOTMP | $^{227}$Th-DOTMP | $^{227}$Th-DTMP |
|---|---|---|---|---|
| Femur/Blood | 129 | >196 | >196 | >196 |
| Femur/Liver | 29.1 | 16.4 | 52.7 | 49 |
| Femur/Spleen | 6.4 | 41.3 | 40.3 | 151 |
| Femur/Kidneys | 6.4 | 7.7 | 6.0 | 14.2 |

Thus although actinium and thorium as cations do not possess sufficient selectivity for bone, it is possible to prepare bone seeking radiopharmaceuticals with suitable bone to soft tissue ratios for therapeutic targeting of skeletal surfaces by combining actinium and/or thorium radioisotopes with, e.g. polyphosphonates with sufficient complexing strength. These compounds may have an even more rapid clearance from soft tissues compared with the alkaline earth bone seeker radium-223.

The invention claimed is:

1. A method of radiation treatment of a human or non-human mammalian subject which comprises administering to said subject a therapeutic, prophylactic or pain-palliating amount of a bone-targeting complex of an alpha-particle emitting actinium radionuclide and a bisphosphonate or polyphosphonate ligand.

2. A method as claimed in claim 1 wherein said complex is administered parenterally by injection or infusion.

3. A method as claimed in claim 1, wherein said radionuclide is actinium-225.

4. A method as claimed in claim 1, wherein said method is a method of therapeutic treatment of a disease affecting a soft tissue.

5. A method as claimed in claim 1, wherein said method is a method of therapeutic treatment of a disease affecting a bone.

6. A method as claimed in claim 1, wherein said method is a method of pain palliation of a disease affecting a soft tissue.

7. A method as claimed in claim 1, wherein said method is a method of pain palliation of a disease affecting a bone.

8. A radiopharmaceutical composition comprising a bone-targeting complex of an alpha-particle emitting actinium radionuclide with a bisphosphonate or polyphosphonate ligand, and a physiologically acceptable carrier or excipient.

9. A composition as claimed in claim 8 wherein said radionuclide is actinium-225.

10. A bone-targeting complex comprising an alpha-particle emitting actinium radionuclide and a bisphosphonate or polyphosphonate ligand.

11. A kit for the treatment of a bone surface or a primary or a metastatic cancer to the skeleton, said kit comprising, an alpha-particle emitting actinium radioisotope, a bisphosphonate or polyphosphonate bone seeking chelator, and a pharmaceutically acceptable carrier.

12. A kit as claimed in claim 11, wherein said kit further comprises administration equipment.

* * * * *